United States Patent [19]

Shroot et al.

[11] Patent Number: 4,708,959
[45] Date of Patent: Nov. 24, 1987

[54] 4,5-TRIMETHYLENE-4-ISOTHIAZOLINE-3-ONES AND THEIR USE AS A BACTERICIDE AND FUNGICIDE AGENT

[75] Inventors: Braham Shroot, Antibes; Jean Maignan, Tremblay les Gonesse, both of France

[73] Assignee: Centre International de Recherches Dermatologiques (C.I.R.D.), Valbonne, France

[21] Appl. No.: 517,749

[22] Filed: Jul. 27, 1983

Related U.S. Application Data

[63] Continuation-in-part of Ser. No. 311,400, Oct. 14, 1981, abandoned.

[30] Foreign Application Priority Data

Oct. 17, 1980 [FR] France .................. 80 22278

[51] Int. Cl.$^4$ .................. A61K 31/425; C07D 275/04
[52] U.S. Cl. .................. 514/373; 544/168; 548/209; 564/189
[58] Field of Search .............. 548/209, 213; 424/270; 514/373

[56] References Cited

U.S. PATENT DOCUMENTS

| | | | |
|---|---|---|---|
| 3,562,283 | 2/1971 | Lewis et al. | 548/213 |
| 3,761,488 | 9/1973 | Lewis et al. | 548/213 |
| 3,950,349 | 4/1976 | Buckley et al. | 548/209 |

FOREIGN PATENT DOCUMENTS

| | | | |
|---|---|---|---|
| 234383 | 9/1959 | Australia | 548/209 |
| 179697 | 4/1986 | European Pat. Off. | 548/209 |
| 1113634 | 5/1968 | United Kingdom | 424/270 |

Primary Examiner—Donald G. Daus
Assistant Examiner—D. Rivers
Attorney, Agent, or Firm—Cushman, Darby & Cushman

[57] ABSTRACT

A 4,5-trimethylene-4-isothiazoline-3-one of the formula

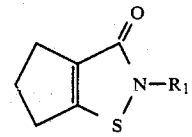

wherein $R_1$ represents (i) hydrogen, (ii) alkyl having 1–12 carbon atoms, (iii) alkyl having 2 or 3 carbon atoms and substituted by one or two hydroxy groups, (iv) alkenyl having 3 to 6 carbon atoms, (v)

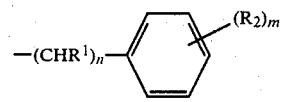

wherein n is 0 or 1, m is 1 or 2, $R^1$ is hydrogen or lower alkyl having from 1 to 5 carbon atoms and $R_2$ is hydrogen, lower alkyl, nitro, trifluoromethyl or halogen, (vi) cycloalkyl having 3 to 6 carbon atoms and (vii)

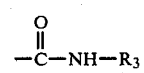

wherein $R_3$ is hydrogen, alkyl having 1–12 carbon atoms or

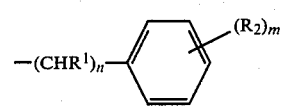

defined above, or the salt thereof with a mineral or organic acid. These compounds are useful as bactericides or fungicides.

17 Claims, No Drawings

4,5-TRIMETHYLENE-4-ISOTHIAZOLINE-3-ONES AND THEIR USE AS A BACTERICIDE AND FUNGICIDE AGENT

This application is a continuation-in-part of our application, Ser. No. 311,400, filed Oct. 14, 1981 now abandoned.

The present invention relates to new chemical compounds belonging to the group of 4,5-trimethylene-4-isothiazoline-3-ones and to a process for their preparation and use as bactericides and fungicides.

The 4,5-trimethylene-4-isothiazoline-3-ones in accordance with the invention can be represented by the following formula.

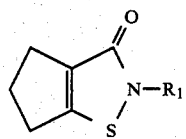

(I)

wherein $R_1$ represents (i) hydrogen, (ii) a linear or branched alkyl having from 1 to 12 carbon atoms, (iii) a linear or branched alkyl having from 2 to 3 carbon atoms substituted by one or two hydroxyl groups, (iv) an alkenyl having from 3 to 6 carbon atoms, (v) a radical of the formula

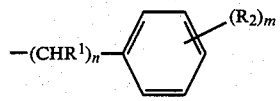

wherein n is 0 or 1, m is 1 or 2, $R^1$ represents hydrogen or a lower alkyl having from 1 to 5 carbon atoms and $R_2$ represents hydrogen, lower alkyl having from 1–5 carbon atoms, nitro, trifluoromethyl or halogen, preferably Cl, Br or I, (vi) cycloalkyl having from 3 to 6 carbon atoms and (vii) a radical of the formula

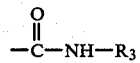

wherein $R_3$ represents hydrogen, linear or branched alkyl having from 1 to 12 carbon atoms or a radical of the formula

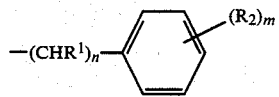

such as defined above, and their salts of a mineral or organic acid.

When $R_1$ in formula (I) above, represents a linear or branched alkyl, the alkyl moiety can be, for instance, methyl, ethyl, propyl, isopropyl, butyl, isobutyl, tert. butyl, hexyl, octyl or dodecyl.

When $R_1$ represents alkyl having from 2 to 3 carbon atoms substituted by one or two hydroxyl groups, this group can be, for instance, 2-hydroxyethyl, 2-hydroxypropyl or 1,2-dihydroxypropyl.

When $R_1$ represents alkenyl, the substituent can be, for example, an allyl radical.

When $R_1$ represents a radical of the formula

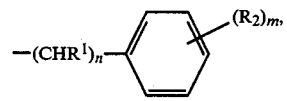

it can be, for instance, phenyl, p-chlorophenyl, 2,4-dichlorophenyl, benzyl, p-chlorobenzyl or 2,4-dichlorobenzyl.

When $R_1$ represents cycloalkyl having from 3 to 6 carbon atoms, it can be cyclopropyl, cyclobutyl, cyclopentyl or cyclohexyl.

Finally, when $R_1$ represents a radical of the formula

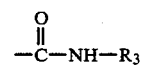

it can be carbamoyl, N-methyl carbamoyl, N-ethyl carbamoyl, N-isopropyl carbamoyl, N-propyl carbamoyl, N-phenyl carbamoyl, N-cyclohexyl carbamoyl, N-butyl carbamoyl or N-octyl carbamoyl.

When in the compounds according to the present invention $R_1$ represents hydrogen, these compounds can have the 3-hydroxy isothiazole type structure.

These compounds can then be provided under one or both of the following tautomeric forms:

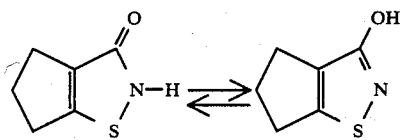

Representative salts of the new 4,5-trimethylene-4-isothiazoline-3-ones according to the invention include, in particular, the hydrochlorides, hydrobromides, nitrates, sulfates and succinates thereof.

Representative compounds of the present invention which correspond to formula (I) above, include, in particular, the following:

| Compound No. | | $R_1$ | Salt |
| --- | --- | --- | --- |
| (1) | 4,5-trimethylene-4-isothiazoline-3-one | H | HCl (1a) |
| (2) | 2-methyl-4,5-trimethylene-4-isothiazoline-3-one | $-CH_3$ | HCl (2a) |
| (3) | 2-ethyl-4,5-trimethylene-4-isothiazoline-3-one | $-C_2H_5$ | |
| (4) | 2-propyl-4,5-trimethylene-4-isothiazoline-3-one | $-_nC_3H_7$ | |
| (5) | 2-isopropyl-4,5-trimethylene-4-isothiazoline-3-one | $-isoC_3H_7$ | HCl (5a) |
| (6) | 2-butyl-4,5-trimethylene-4-isothiazoline-3-one | $-_nC_4H_9$ | HCl (6a) |

-continued

| Compound No. | | R₁ | Salt |
|---|---|---|---|
| (7) | 2-isobutyl-4,5-trimethylene-4-isothiazoline-3-one | isoC₄H₉ | |
| (8) | 2-tert.butyl-4,5-trimet-ylene-4-isothiazoline-3-one | tert.C₄H₉ | |
| (9) | 2-hexyl-4,5-trimethylene-4-isothiazoline-3-one | —C₆H₁₃ | |
| (10) | 2-octyl-4,5-trimethylene-4-isothiazoline-3-one | —C₈H₁₇ | |
| (11) | 2-cyclohexyl-4,5-trimethylene-4-isothiazoline-3-one | —cyclohexyl | |
| (12) | 2-phenyl-4,5-trimethylene-4-isothiazoline-3-one | —phenyl | |
| (13) | 2-(4-chlorophenyl)-4,5-trimethylene-4-isothiazoline-3-one | —p.chlorophenyl | |
| (14) | 2-(2,4-dichlorophenyl)-4,5-trimethylene-4-isothiazoline-3-one | 2,4-dichlorophenyl | |
| (15) | 2-benzyl-4,5-trimethylene-4-isothiazoline-3-one | benzyl | |
| (16) | 2-(4-chlorobenzyl)-4,5-trimethylene-4-isothiazoline-3-one | p-chlorobenzyl | |
| (17) | 2-(2,4-dichlorobenzyl)-4,5-trimethylene-4-isothiazoline-3-one | 2,4-dichlorobenzyl | |
| (18) | 2-(2-hydroxyethyl)-4,5-trimethylene-4-isothiazoline-3-one | —CH₂CH₂OH | |
| (19) | 2-(2-hydroxypropyl)-4,5-trimethylene-4-isothiazoline-3-one | —CH₂—CHOH—CH₃ | |
| (20) | 2-(2,3-dihydroxypropyl)-4,5-trimethylene-4-isothiazoline-3-one | —CH₂—CHOH—CH₂OH | |
| (21) | 2-allyl-4,5-trimethylene-4-isothiazoline-3-one | —CH₂—CH=CH₂ | |
| (22) | 2-carbamoyl-4,5-trimethylene-4-isothiazoline-3-one | —CONH₂ | |
| (23) | 2-N—methylcarbamoyl-4,5-trimethylene-4-isothiazoline-3-one | —CONH—CH₃ | |
| (24) | 2-N—ethylcarbamoyl-4,5-trimethylene-4-isothiazoline-3-one | —CONH—C₂H₅ | |
| (25) | 2-N—isopropylcarbamoyl-4,5-trimethylene-4-isothiazoline-3-one | —CONH—isoC₃H₇ | |
| (26) | 2-N—butylcarbamoyl-4,5-trimethylene-4-isothiazoline-3-one | —CONH—ₙC₄N₉ | |
| (27) | 2-N—pentylcarbamoyl-4,5-trimethylene-4-isothiazoline-3-one | —CONHC₅H₁₁ | |
| (28) | 2-N—heptylcarbamoyl-4,5-trimethylene-4-isothiazoline-3-one | —CONHC₇H₁₅ | |
| (29) | 2-N—nonylcarbamoyl-4,5-trimethylene-4-isothiazoline-3-one | —CONHC₉H₁₉ | |
| (30) | 2-N—phenylcarbamoyl-4,5-trimethylene-4-isothiazoline-3-one | —CONHC₆H₅ | |
| (31) | 2-N—cyclohexylcarbamoyl-4,5-trimethylene-4-isothiazoline-3-one | —CONHC₆H₁₁ | |

The compounds according to the present invention can be prepared by various processes and principally by the process described by Goerdeler and Mittler, Chem. Ber., 96, 944–954 (1963) which consists in oxidizing, in an inert organic solvent medium, a 2-carbamoyl thiocyclopentanone (2) in accordance with the following reaction scheme.

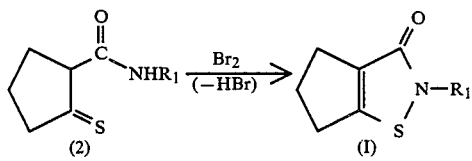

The preparation of the compounds according to the invention has however been carried out using a new process comprising (a) in a first stage sulfurating a 2-carbamoyl cyclopentanone of the formula

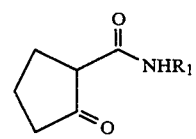

to produce a 2-carbamoyl thiocyclopentanone in its tautomeric forms,

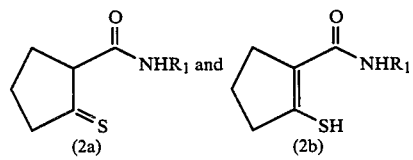

in an anhydrous alcohol solution saturated with HCl gas by means of a current of H₂S and HCl gas and (b) in a second stage treating the resulting alcoholic solution of 2-carbamoyl thiocyclopentanone with sodium metaperiodate previously fixed on acidic alumina. This process can be represented by the following reaction scheme:

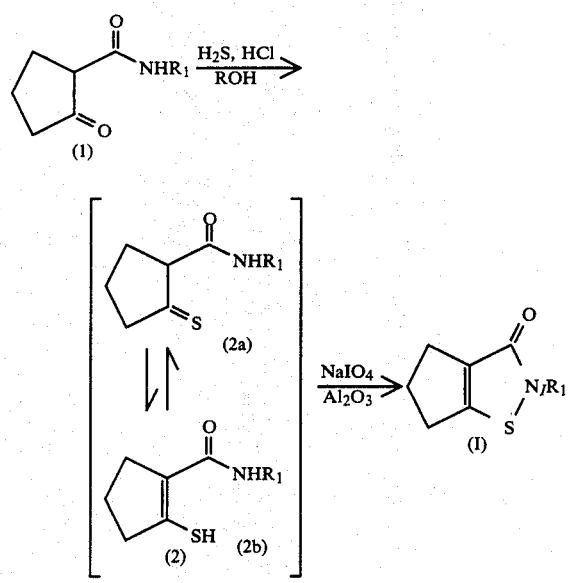

The first stage wherein the 2-carbamoyl cyclopentanone is sulfurated can be carried out at a temperature lower than or equal to 0° C. for at least 5 hours. In the second stage, there is employed 0.5 molar equivalent of the sodium metaperiodate fixed on acidic alumina.

This process provides the compounds of the present invention in good yields and in a relatively pure form.

The preparation of the sodium metaperiodate fixed on acidic alumina has been described by Kwang-Ting Liu and Yung-Chien Tong, J. Org. Chem. 43, 2717-2718 (1978).

It will be noted that, according to the present invention, it is not necessary to add a molar equivalent of sodium metaperiodate; in effect a half molar equivalent generally suffices.

This can be explained by the fact that the medium being very strongly acidic, iodine is liberated which completes the oxidation of the 4-isothiazoline-3-one.

At the end of the reaction, the alumina is filtered then washed with alcohol (methanol or ethanol) and the alcoholic phases are combined and then concentrated under reduced pressure.

The residue obtained after evaporation can be, if desired, taken up in an appropriate solvent such as chloroform, ethyl acetate, benzene or ether and then either directly fractionated by chromatography on silica gel or alumina column, or treated with vigorous agitation by an aqueous phase, the pH of which is adjusted to about 5 by the addition thereto of sodium carbonate. The organic phase, after decanting, is dried on sodium sulfate and the 4-isothiazoline-3-one is then isolated by fractionation on silica gel or simply directly under the form of its hydrochloride by passing a current of gaseous HCl into the solution.

Thus, as noted above, the 2-carbamoyl thiocyclopentanones (2) are obtained from 2-carbamoyl cyclopentanones (1) by a sulfuration reaction, in an anhydrous alcoholic solution saturated with HCl gas, by means of a simultaneous current of $H_2S$ and HCl gas for at least about 5 hours.

During the reaction, the reaction mixture is maintained at a temperature lower than or equal to 0° C.

Although it is possible to isolate the 2-carbamoyl thiocyclopentanones (2), it is preferred, in accordance with the invention, after the sulfuration reaction, to directly treat the reaction mixture, after previously de-gassing it, with sodium metaperiodate fixed on acidic alumina.

The 2-carbamoyl cyclopentanones (1) with $R_1$ being equal to hydrogen can be obtained by the method described by Ch. Bischoff and H. Herma, J. F. Prakt. Chemie, 318, 773-778 (1976) which consists in reacting urea with cyclopentanone in toluene heated to the boil in the presence of p-toluene sulfonic acid, the intermediate compound thus obtained being then hydrolyzed by sulfuric or hydrochloric acid.

The 2-carbamoyl cyclopentanones (1) with $R_1 \neq H$ can be prepared according to the method described by S. Hunig et al, Chem. Ber., 95, 926-936 (1962) which consists in reacting an N-substituted isocyanate on an enamine (3) and hydrolyzing the resulting addition product (4) in an acid medium.

This method can be represented by the following reaction scheme:

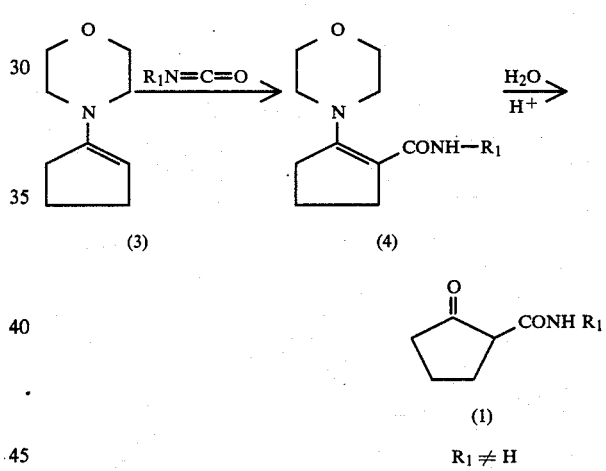

According to a preferred embodiment of the invention, the 4,5-trimethylene-4-isothiazoline-3-ones in which the $R_1$ radical represents linear or branched alkyl having at least two carbon atoms and being substituted by one or more hydroxyl groups are prepared by reacting 4,5-trimethylene-4-isothiazoline-3-one(I)($R_1$=H) with an oxirane, substituted or not, with a basic catalyst which leads to 4,5-trimethylene-4-isothiazoline-3-ones substituted at the 2-position by a mono- or poly-hydroxyalkyl radical. This reaction can be represented by the following reaction scheme:

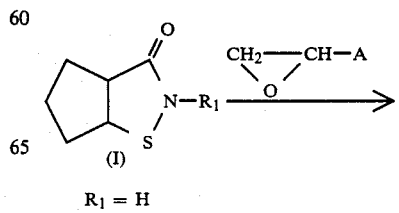

-continued

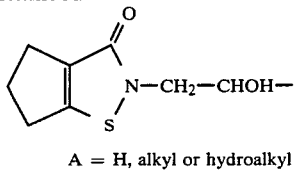

A = H, alkyl or hydroalkyl

Also, when in the 4,5-trimethylene-4-isothiazoline-3-ones the $R_1$ radical represents a carbamoyl or N-substituted carbamoyl radical, ($R_1 = -CONHR_3$), these compounds are preferably prepared by reacting a 4,5-trimethylene-4-isothiazoline-3-one ($R_1 = H$) with an N-substituted isocyanate with a basic catalyst according to the following reaction scheme:

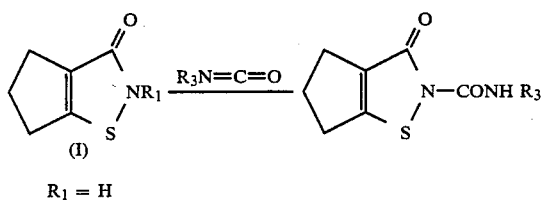

$R_1 = H$

The salts of the 4,5-trimethylene-4-isothiazoline-3-ones with strong mineral or organic acids can be prepared by dissolving the compounds to be salified in an inert organic solvent such as ether, chloroform or ethyl acetate and then adding the acid, either pure or in solution or even by bubbling in the case of HBr or HCl.

After precipitation and eventually cooling the solution, it is filtered and the resulting salt is recrystallized in an appropriate solvent.

It is noted, however, that when the process for preparing 4,5-trimethylene-4-isothiazoline-3-ones is carried out in HCl siolution, the compounds are obtained directly under the form of their hydrochloride when the process occurs at the end of a chromatography reaction. However, because of the instability, for the most part of these compounds, the 4,5-trimethylene-4-isothiazoline-3-ones are obtained in their free form.

The 4,5-trimethylene-4-isothiazoline-3-ones according to the invention exhibit good anti-bacteria, antifungus and anti-acne activity.

These compounds act not only on gram positive bacteria but also on gram negative bacteria, yeasts and molds.

Consequently the present invention also relates to a cosmetic composition comprising in a cosmetically acceptable carrier an effective amount of the 4,5-trimethylene-4-isothiazoline-3-ones or an acid addition salt thereof. Preferably the 4,5-trimethylene-4-isothiazoline-3-one or its acid addition salt is present in an amount ranging from 0.1 to 10 percent by weight based on the total weight of the composition. The carrier can be a solid, semi-solid or liquid vehicle.

Representative solid substances which can be used as carriers or vehicles appropriate for the preparation of compositions under the form of powders, include various porous and pulverulent agents of an organic or non-organic nature, such as tricalcium phosphate, calcium carbonate, kaolin, bentonite, talc, kieselguhr, boric acid, powdered cork, sawdust and other fine pulverulent materials of vegetable origin.

The active ingredient is mixed with the substances employed as the carrier, for example, by being pulverized with them. As a variation, the inert material used as the carrier or vehicle, can be impregnated with a solution of an active component in an easily volatilized solvent and the solvent is then eliminated by heating or by filtration with aspiration under reduced pressure. By adding wetting and/or dispersing agents to the pulverulent preparation, which can be easily moistened with water, suspensions can be obtained.

The inert solvents used for the preparation of liquid compositions must be, non-flammable, odorless and non-toxic vis-a-vis warm blooded animals and plants.

It is also possible to use a mixture of solvents. Other liquid forms that can be employed include emulsions or suspensions of an active component in water or conventional inert solvents. Moreover, concentrates, for the preparation of these emulsions, which can be directly adjusted to the desired concentration can be employed. To this end, the active component is, for example, admixed with a dispersing or emulsifying agent. The active component can also be dissolved or dispersed in an appropriate inert solvent and admixed simultaneously or subsequently with a dispersing or emulsifying agent.

It is also possible to use semi-solid carriers or vehicles and, in particular, a creamy ointment or a paste in which the active component is incorporated.

Besides, it is also possible to employ the active components of the present invention in the form of aerosols. The active component is, in this case, dissolved or dispersed in an appropriate inert solvent. There are thus produced solutions, under pressure, which when they are sprayed provide aerosols which are particularly effective in combatting against microorganisms.

The above-mentioned compositions can be applied by conventional methods such as by powdering, aspersion, spraying, brushing, dipping, coating, impregnation, absorption, injection or by any other appropriate means.

The 4,5-trimethylene-4-isothiazoline-3-ones or their salts, according to the present invention, can be used in cosmetics and act, for example, as a preservative in such compositions as shampoos, capillary lotions, deodorants, sunscreen products, face and body products and the like.

The 4,5-trimethylene-4-isothiazoline-3-ones can also be used as the active principle in cosmetic compositions provided in the form of solutions, dispersions, emulsions, creams, gels, pastes, aerosols, powders or soaps.

The present invention also relates to pharmaceutical compositions for human or veterinary use comprising an effective amount of said 4,5-trimethylene-4-isothiazoline-3-one in a pharmaceutically acceptable vehicle. When so employed the 4,5-trimethylene-4-isothiazoline-3-one can be present in an amount ranging from 0.1 to 10 percent by weight based on the total weight of said composition.

These compositions can be provided in the form of a solution, emulsion, suspension, cream, lotion, ointment, aerosol, powder, in the form of injectable solutions or suspensions, tablets, granules or capsules and can be administered in accordance with the type of formulation i.e. topically or by any other general method.

Good activity for these compounds over a very wide range of dilutions has been observed. For example, concentrations of the active component ranging from 0.1 to 10 weight percent, calculated on the weight of the composition employed, have proved effective. However, it is possible to use higher concentrations when this is necessary for a particular application.

The technique employed to determine good bacteria activity consists in using the known method of diffusion with pellets.

The compounds of the present invention have been shown to be particularly effective against the following bacteria: *Escherichia coli, Pseudomonas aeruginosa, Bacillus subtilis, Staphylococcus aureus, Sarcina lutea, Candida lypolytica* and *Aspergillus niger.*

As an example, 4,5-trimethylene-4-isothiazoline-3-one, dissolved at 0.5% in propylene glycol, exhibits zones of inhibition, expressed in millimeters as follows:
gram negative:
  *Escherichia coli*, 30
  *Pseudomonas aeruginosa*, 20
gram positive:
  *Bacillus subtilis*, 37
  *Staphylococcus aureus*, 30
  *Sarcina lutea*, >40
Yeasts:
  *Candida lypolytica*, 12
Molds:
  *Aspergillus niger*, 22

The compounds according to the present invention can be used in different fields of industry such as agriculture, paper-making, paint and enamels, cosmetics, pharmaceuticals, human or veterinary and the like.

The following non-limiting examples are given to illustrate the preparation of the new compounds of the present invention.

EXAMPLE 1

Preparation of 4,5-trimethylene-4-isothiazoline-3-one (No. 1)

8.5 g of 2-carbamoyl cyclopentanone are dissolved in 100 cc of anhydrous methanol saturated with gaseous HCl and cooled to 0° C. There is then passed into the solution a current of $H_2S$ and gaseous HCl for about 6 hours. Then after having de-gassed the reaction mixture there is added, with agitation at 0° C., 0.5 molar equivalent of sodium metaperiodate fixed on acidic alumina.

After continued agitation for about one-half hour, the alumina is filtered, then washed with methanol. The methanolic phases are evaporated under reduced pressure and the residue is taken up in boiling ethyl acetate.

After cooling, the 4,5-trimethylene-4-isothiazoline-3-one crystallizes. After filtering and recrystallizing in an ethyl acetate-ethanol mixture, a beige solid exhibiting a melting point of about 190° C. is obtained.

| Analysis: | $C_6H_7NOS$ | | | |
|---|---|---|---|---|
| Calculated: | C - 51.04 | H - 5.00 | N - 9.92 | S - 22.71 |
| Found: | 50.59 | 5.03 | 10.26 | 22.36 |

EXAMPLE 2

Preparation of 4,5-trimethylene-4-isothiazoline-3-one hydrochloride (No. 1a)

To a solution of 3.8 g of 4,5-trimethylene-4-isothiazoline-3-one, prepared in accordance with Example 1, in 250 cc of chloroform there are added, with agitation, 13 cc of a solution of 2N HCl in ether. The desired hydrochloride precipitates, is filtered and dried under reduced pressure at a temperature lower than 50°. 2.8 g of the desired hydrochloride having a white color and a melting point of 168° C. are obtained.

| Analysis: | $C_6H_8ClNOS$ | | |
|---|---|---|---|
| Calculated: | C - 40.56 | H - 4.54 | N - 7.88 |
| Found: | 40.32 | 4.69 | 7.76 |

EXAMPLE 3

Preparation of 2-methyl-4,5-trimethylene-4-isothiazoline-3-one (No. 2)

5 g of 2-(N-methylcarbamoyl)cyclopentanone are dissolved in 100 cc of anhydrous ethanol saturated by anhydrous HCl gas. Into this solution, cooled to 0° C., there is passed for 5 hours a current of $H_2S$ and HCl gas. After having de-gassed the reaction mixture, there is added, with agitation, 0.5 molar equivalent of sodium metaperiodate fixed on acidic alumina ($Al_2O_3$), the temperature being maintained at 0° C. One-half hour later the reaction mixture is filtered. The filtrate is concentrated under reduced pressure. The residue is taken up in a 1:1 mixture of ethyl acetate and water. The pH of the aqueous solution is then adjusted, with agitation, to about 6 by the addition of sodium bicarbonate. The aqueous phase is decanted, then extracted with chloroform. The chloroform phase is then dried on sodium sulfate, and concentrated. On evaporation, an amorphous white solid, melting at 111° C. is obtained. Mass spectroscopy gives the expected relative peak at m/e: 155 ($C_7H_9NOS$)

| | Analysis: $C_7H_9NOS$ | | | | |
|---|---|---|---|---|---|
| Calculated: | C - 54.16 | H - 5.84 | N - 9.02 | O - 10.31 | S - 20.66 |
| Found: | 54.18 | 5.82 | 9.13 | 10.27 | 20.82 |

EXAMPLE 4

Preparation of 2-isopropyl-4,5-trimethylene-4-isothiazoline-3-one (No. 5a)

3.5 g of 2-N-isopropylcarbamoyl cyclopentanone are dissolved in 50 cc of anhydrous ethanol saturated by HCl gas and $H_2S$. There is then passed into this solution, maintained at 0° C., a current of $H_2S$ and HCl gas for about 6 hours. After de-gassing the solution, there is added, with agitation and always at 0° C., 0.5 molar equivalent of sodium metaperiodate fixed on acidic alumina. The reaction mixture is filtered. The filtrate is concentrated under reduced pressure and taken up in a water-ethyl acetate mixture. To this agitated mixture, sodium bicarbonate is slowly added to adjust the pH of the aqueous phase to about 5.5.

The ethyl acetate phase is decanted, dried on sodium sulfate and then concentrated. 5.8 g of a viscous brown liquid is obtained which is taken up in a minimum of chloroform.

The chloroform phase is deposited on a silica gel column; 2-isopropyl-4,5-trimethylene-4-isothiazoline-3-one is eluted with a 3:2 mixture of chloroform:benzene and isolated in liquid form.

This is dissolved in ether; a current of HCl gas is passed into the solution and the expected product precipitates in the hydrochloride form. This latter is filtered, then recrystallized in a benzene-ether mixture. A white solid having a melting point of 76° C. is obtained, the elemental analysis of which corresponds to a monohydrate.

| Analysis: C$_9$H$_{14}$ClNOS.1H$_2$O | | | | |
|---|---|---|---|---|
| Calculated: | C - 45.46 | H - 6.78 | Cl - 14.91 | S - 13.49 |
| Found: | 46.08 | 6.50 | 15.19 | 13.67 |

EXAMPLE 5

Preparation of 2-butyl-4,5-trimethylene-4-isothiazoline-3-one (No. 6a)

5.6 g of 2-(N-butylcarbamoyl)cyclopentanone are dissolved in 100 cc of anhydrous methanol saturated by HCl gas and cooled to 0° C.

A current of H$_2$S and HCl gas is passed into the solution for about 6 hours. After having de-gassed the reaction mixture, a 0.5 molar equivalent of sodium periodate fixed on acidic alumina is added under agitation, at 0° C.

After continued agitation for one-half hour, the alumina is filtered and then washed with methanol. The methanolic solution is then passed over silica gel and then by chromatography on neutral alumina.

After evaporation under reduced pressure of the chromatography solvent the 2-butyl-4,5-trimethylene-4-isothiazoline-3-one is dissolved in ethyl ether through which is bubbled HCl gas.

The resulting hydrochloride is decanted in the form of a crude oil. After evaporation of the ether and taking up of the residue in an ethanol-isopropyl ether mixture, the hydrochloride is provided in the form of a white solid having a melting point of 112°–113° C.

| Analysis: C$_{10}$H$_{16}$ClNOS | | | | |
|---|---|---|---|---|
| Calculated: | C - 51.38 | H - 6.90 | Cl - 15.17 | N - 5.99 | S - 13.71 |
| Found: | 51.16 | 7.27 | 15.31 | 6.22 | 13.82 |

EXAMPLE 5'

Preparation of 2-n-butyl-4,5-trimethylene-4-isothiazoline-3-one (No. 6)

To a suspension of 3.50 g of 2-butyl-4,5-trimethylene-4-isothiazoline-3-one hydrochloride (described in Example 5) in 50 cc of ethyl ether, agitated and protected from light, at ambient temperature and under an inert atmosphere, there is added, all at once, one equivalent of triethylamine. One hour later the triethylamine hydrochloride is filtered. The filtrate is washed with water. The ether phase is dried on sodium sulfate, then concentrated under reduced pressure. After drying on phosphoric anhydride, under a vaccum, 2.3 g of 2-butyl-4,5-trimethylene-4-isothiazoline-3-one are obtained. It is a clear yellow liquid at ambient temperature.

| Analysis: C$_{10}$H$_{15}$NOS | | | | |
|---|---|---|---|---|
| Calculated: | C - 60.88 | H - 7.66 | N - 7.10 | O - 8.11 | S - 16.25 |
| Found: | 61.00 | 7.67 | 7.18 | 8.20 | 16.23 |

EXAMPLE 6

Preparation of 2-octyl-4,5-trimethylene-4-isothiazoline-3-one (No. 10)

This compound is prepared according to the process of example 3 above.

On evaporation light brown crystals are obtained melting below 50° C.

| Analysis: C$_{14}$H$_{23}$NOS | | | | |
|---|---|---|---|---|
| Calculated: | C - 66.36 | H - 9.15 | N - 5.43 | O - 6.31 | S - 12.65 |
| Found: | 66.35 | 9.10 | 5.26 | 6.60 | 12.30 |

EXAMPLE 7

Preparation of 2-cyclohexyl-4,5-trimethylene-4-isothiazoline-3-one (No. 11)

This compound is prepared according to the process of example 3 above.

On evaporation beige crystals are obtained melting at 70° C.

| Analysis: C$_{12}$H$_{17}$NOS | | | | |
|---|---|---|---|---|
| Calculated: | C - 64.53 | H - 7.67 | N - 6.27 | O - 7.17 | S - 14.36 |
| Found: | 64.63 | 7.72 | 6.19 | 7.15 | 14.11 |

EXAMPLE 8

Preparation of 2-phenyl-4,5-trimethylene-4-isothiazoline-3-one (No. 12)

A solution of 1 g of 2-(N-phenylcarbamoyl)cyclopentanone, in 20 cc of anhydrous ethanol, cooled to 0° C. is added to 10 cc of anhydrous ethanol saturated by HCl gas and H$_2$S and cooled to 0° C. while maintaining this temperature, there is passed into the solution a current of H$_2$S and HCl gas for about 3 hours. After having de-gassed the reaction mixture, 0.5 molar equivalent of sodium metaperiodate fixed on acidic alumina is added with agitation at 0° C. The agitation is continued for about one-half hour; the alumina is then filtered and washed with ethanol. The filtrate is concentrated under reduced pressure and the resulting residue is taken up in water. To the resulting suspension there is added, with agitation, sufficient sodium bicarbonate until a pH of 5 is obtained.

The 2-phenyl-4,5-trimethylene-4-isothiazoline-3-one, insoluble in the medium, is filtered, dissolved in a minimum of chloroform, then deposited on a silica gel column. The expected product is eluted with a 5:3:2 benzene:chloroform:ethyl acetate mixture. After evaporation of this solution, the product is isolated in the form of a beige solid having a melting point of 175° C.

| Analysis: C$_{12}$H$_{11}$NOS | | | | |
|---|---|---|---|---|
| Calculated: | C - 66.33 | H - 5.10 | N - 6.45 | O - 7.36 | S - 14.76 |
| Found: | 66.49 | 5.22 | 6.40 | 7.45 | 14.48 |

EXAMPLE 9

Preparation of 2-(4-chlorophenyl)-4,5-trimethylene-4-isothiazoline-3-one (No. 13)

This compound is prepared according to the process of example 8 above.

After evaporation, the product is isolated in the form of a light beige solid having a melting point of 177° C.

| Analysis: $C_{12}H_{10}ClNOS$ | | | | | | |
|---|---|---|---|---|---|---|
| Calculated: | C - 57.25 | H - 4.00 | Cl - 14.08 | N - 5.46 | O - 6.35 | S - 12.74 |
| Found: | 57.21 | 3.97 | 13.86 | 5.52 | 6.56 | 12.82 |

EXAMPLE 10

Preparation of 2-(4-chlorobenzyl)-4,5-trimethylene-4-isothiazoline-3-one (No. 16)

This compound is prepared according to the process of example 8 above.

After evaporation, the product is isolated in the form of light grey needles having a melting point of 105° C.

| Analysis: $C_{13}H_{12}ClNOS$ | | | | | | |
|---|---|---|---|---|---|---|
| Calculated: | C - 58.75 | H - 4.55 | Cl - 13.34 | N - 5.27 | O - 6.02 | S - 12.06 |
| Found: | 58.55 | 4.52 | 13.29 | 5.21 | 6.20 | 12.15 |

EXAMPLE 11

Preparation of 2-(2,3-dihydroxypropyl)-4,5-trimethylene-4-isothiazoline-3-one (No. 20)

To a solution of 0.7 g of 4,5-trimethylene-4-isothiazoline-3-one, such as obtained in accordance with Example 1, in 20 cc of anhydrous toluene there is added, all at once, an excess of glycidol (0.86 g), then a drop of 1,5-diaza-5-bicyclo[5.4.0]undecene (D.B.U.). The reaction mixture is then heated to the boiling temperature of the solvent for 8 hours.

The solvent is then evaporated under reduced pressure. The residue is taken up in a minimum of chloroform which is then deposited on a silica gel column,. The expected product is fixed with hexane and finally directly eluted with a 5:2:1 isopropyl ether:ethyl acetate:isopropanol mixture. The oil obtained, taken up in anhydrous ethyl ether, gives a beige powder having a melting point of 100 C.

| Analysis: $C_9H_{13}NO_3S$ | | | | |
|---|---|---|---|---|
| Calculated: | C - 50.21 | H - 6.09 | N - 6.51 | S - 14.89 |
| Found: | 50.10 | 6.35 | 6.65 | 14.90 |

EXAMPLE 12

Preparation of 2-N-methylcarbamoyl-4,5,-trimethylene-4-isothiazoline-3-one (No. 23)

To a suspension of 0.750 g of 4,5-trimethylene-4-isothiazoline-3-one hydrochloride, obtained in accordance with Example 2, in 30 cc of anhydrous tetrahydrofuran (THF), agitated at ambient temperature, under an inert atmosphere protected from light and the humidity of the air there is added, all at once, 0.426 g (1 equivalent) of triethylamine. Ten minutes later one equivalent of methyl isocyanate is added. One hour later the reaction is terminated. The triethylamine hydrochloride is filtered and washed with tetrahydrofuran. The filtrate is concentrated under reduced pressure. The resulting solid is dissolved in a minimum of benzene and then deposited on a silica gel chromatography column. The expected product is eluted with a benzene-chloroform mixture and then crystallized in a benzene-hexane mixture. 0.8 g of white crystals having a melting point of 167° C. is obtained.

| Analysis: $C_6H_{10}N_2O_2S$ | | | | |
|---|---|---|---|---|
| Calculated: | C - 48.46 | H - 5.08 | N - 14.31 | O - 16.14 | S - 16.17 |
| Found: | 48.42 | 5.11 | 14.31 | 16.03 | 16.10 |

EXAMPLE 13

Preparation of 2-N-butylcarbamoyl-4,5-trimethylene-4-isothiazoline-3-one (No. 26)

To a suspension of 0.87 g of 4,5-trimethylene-4-isothiazoline-3-one hydrochloride, obtained in accordance with Example 2, in 30 cc of anhydrous tetrahydrofuran (THF) and agitated at ambient temperature, under an inert atmosphere protected from light and the humidity of the air, there is added, all at once, one equivalent of triethylamine. Ten minutes later 1.2 equivalents of butyl isocyanate are added. The agitation is continued for 15 minutes and then the reaction mixture is permitted to stand overnight. The next day, the triethylamine hydrochloride is filtered and washed with THF. The filtrates are combined and then concentrated under reduced pressure. The residue is taken up in benzene and deposited on a silica gel chromatography column. The expected product is eluted with a 1:1 benzene:chloroform mixture. The resulting solid after concentration of the elution phases is crystallized in petroleum ether. 1 g of white crystals having a melting point of 96° C. is obtained.

| Analysis: $C_{11}H_{16}N_2O_2S$ | | | | | |
|---|---|---|---|---|---|
| Calculated: | C - 54.97 | H - 6.71 | N - 11.65 | O - 13.31 | S - 13.34 |
| Found: | 55.09 | 6.68 | 11.64 | 13.26 | 13.33 |

EXAMPLE 14

Preparation of 2-N-pentylcarbamoyl-4,5-trimethylene-4-isothiazoline-3-one (No. 27)

The reaction is carried out as in Example 13 above, by reacting 2.5 g of 4,5-trimethylene-4-isothiazoline-3-one hydrochloride, treated with one equivalent of triethylamine and then with one equivalent of n-pentyl isocyanate. After removal of the triethylamine hydrochloride, the filtrate is concentrated. The resulting solid is dissolved in toluene and the solution is filtered and then concentrated. There are thus isolated, after having dried the solid, 1.2 g of beige crystals having a melting point of 70° C.

EXAMPLE 15

Preparation of 2-N-heptylcarbamoyl-4,5-trimethylene-4-isothiazoline-3-one (No. 28)

The reaction is carred out as in Example 13 by reacting 2.5 g of 4,5-trimethylene-4-isothiazoline-3-one hydrochloride treated with one equivalent of heptyl isocyanate in the presence of one equivalent of triethylamine.

There are obtained, after recrystallization in hexane, 3.3 g of white crystals having a melting point of 84° C.

| Analysis: $C_{14}H_{22}N_2O_2S$ | | | | |
|---|---|---|---|---|
| Calculated: C - 59.54 | H - 7.85 | N - 9.91 | O - 11.33 | S - 11.35 |
| Found: 59.51 | 7.84 | 9.81 | 11.50 | 11.23 |

EXAMPLE 16

Preparation of 2-N-nonylcarbamoyl-4,5-trimethylene-4-isothiazoline-3-one (No. 29)

By operating in the same manner as disclosed in preceding Examples 13 to 15, 2.5 g of the same initial reactant are reacted with one equivalent of n-nonyl isocyanate in the presence of one equivalent of triethylamine. After recrystallization of the expected product in hexane, 3.7 g of white crystals having a melting point of 87° C. are obtained.

| Analysis: $C_{16}H_{26}N_2O_2S$ | | | | |
|---|---|---|---|---|
| Calculated: C - 61.90 | H - 8.44 | N - 9.02 | O - 10.31 | S - 10.33 |
| Found: 61.87 | 8.51 | 9.07 | 10.42 | 10.19 |

EXAMPLE 17

Preparation of 2-N-cyclohexylcarbamoyl-4,5-trimethylene-4-isothiazoline-3-one (No. 31)

To a suspension of 3.50 g of 4,5-trimethylene-4-isothiazoline-3-one hydrochloride, obtained in accordance with Example 2, in 100 cc of anhydrous tetrahydrofuran (THF) and agitated at ambient temperature under an inert atmosphere protected from light and the humidity of the air, there is added, all at once, one equivalent of triethylamine. Ten minutes later one equivalent of cyclohexyl isocyanate is added. After 2 hours of agitation of ambient temperature, the reaction mixture is permitted to stand overnight. The triethylamine hydrochloride is filtered. The filtrate is concentrated under reduced pressure. The solid thus obtained is dissolved in toluene and the solution is filtered on paper. The expected isothiazoline is precipitated by the addition of hexane.

3.1 g of white crystals having a melting point of 128° C. are obtained.

| Analysis: $C_{13}H_{18}N_2O_2S$ | | | | |
|---|---|---|---|---|
| Calculated: C - 58.62 | H - 6.81 | N - 10.52 | O - 12.01 | S - 12.04 |
| Found: 58.67 | 6.82 | 10.39 | 11.95 | 12.11 |

EXAMPLE I

Non-Ionic Water Suspension

| | |
|---|---|
| 2-N—methyl carbamoyl-4,5 - trimethylene-4-isothiazoline-3-one | 1.00 g. |
| Cetyl alcohol polyoxyethylenated with 20 moles of ethylene oxide | 0.27 g. |
| Stearyl alcohol polyoxyethylenated with 20 moles of ethylene oxide | 0.63 g. |
| Cetyl alcohol | 1.63 g. |
| Stearyl alcohol | 1.47 g. |
| Glycerol monostearate | 1.00 g. |
| Petrolatum oil | 10.00 g. |
| Sterile demineralized water | 84.00 g. |

In this example the active compound can be replaced by the same amount of 2-N-hexylcarbamoyl-4,5-trimethylene-4-isothiazoline-3-one.

EXAMPLE II

Clear Gel

| | |
|---|---|
| 2-N—methylcarbamoyl-4,5-trimethylene-4-isothiazoline-3-one | 0.09 g. |
| Propylene glycol | 30.00 g. |
| Hydroxypropylcellulose | 2.00 g. |
| Water q.s.p. | 100.00 g. |

EXAMPLE III

Ointment

| | |
|---|---|
| 2-N—methylcarbamoyl-4,5-trimethylene-4-isothiazoline-3-one | 1.50 g. |
| Isopropyl myristate | 90.50 g. |
| Silica ("AEROSIL 200" by DEGUSSA Company) | 8.00 g. |

EXAMPLE IV

Gel

| | |
|---|---|
| 2-N—methylcarbamoyl-4,5-trimethylene-4-isothiazoline-3-one | 1.50 g. |
| Ethanol | 30.00 g. |
| Propylene glycol | 30.00 g. |
| Hydroxypropylcellulose | 2.00 g. |
| Water q.s.p. | 100.00 g. |

In this example the active compound can be replaced by the same amount of 4,5 trimethylene-4-isothiazoline-3-one.

EXAMPLE V

Water Washable Ointment

| | |
|---|---|
| 2-N—methylcarbamoyl-4,5-trimethylene-4-isothiazoline-3-one | 0.50 g. |
| Polyethylene glycol 400 | 60.00 g. |
| Polyethylene glycol 4000 | 25.00 g. |
| Petrolatum oil | 14.50 g. |

EXAMPLE VI

Ointment

| | |
|---|---|
| 2-N—nonylcarbamoyl-4,5-trimethylene-4- | 1.00 g. |

-continued

| | |
|---|---|
| isothiazoline-3-one | |
| Triglycerides of caprylic/capric/stearic acids sold under the tradename "SOFTISAN 378" by DYNAMIT NOBEL Company | 50.00 g. |
| Triglycerides of caprylic/capric acids, sold under the tradename "MIGLYOL 812" by DYNAMIT NOBEL Company | 30.00 g. |
| Petrolatum | 19.00 g. |

EXAMPLE VII

Ointment

| | |
|---|---|
| 2-N—ethylcarbamoyl-4,5-trimethylene-4-isothiazoline-3-one | 0.50 g. |
| Triglycerides of caprylic/capric acids sold under the tradename "MYGLIOL 812" | 17.50 g. |
| Isopropyl myristate | 17.50 g. |
| Petrolatum | 49.50 g. |
| Beeswax | 15.00 g. |

EXAMPLE VIII

Suppository

| | |
|---|---|
| 2-N—methylcarbamoyl-4,5-trimethylene-4-isothiazoline-3-one | 0.50 g. |
| Triglycerides of caprylic/capric acids, sold under the tradename "MYGLIOL 812" | 0.20 g. |
| Semi-synthetic glycerides q.s.p. | 2.00 g. |

EXAMPLE IX

Vaginal Ovule

| | |
|---|---|
| 2-N—methylcarbamoyl-4,5-trimethylene-4-isothiazoline-3-one | 0.50 g. |
| Triglycerides of caprylic/capric acids | 0.30 g. |
| Semi-synthetic glycerides q.s.p. | 3.00 g. |

In this example the active compound can be replaced by the same amount of 2-N-ethylcarbamoyl-4,5-trimethylene-4-isothiazoline-3-one or 2-N-nonylcarbamoyl-4,5-trimethylene-4-isothiazoline-3-one.

EXAMPLE X

Tablet For Oral Administration

| | |
|---|---|
| 2-N—methylcarbamoyl-4,5-trimethylene-4-isothiazoline-3-one | 0.25 g. |
| Wheat starch | 0.038 g. |
| Bi-calcium phosphate | 0.1 g. |
| Lactose | .075 g. |
| Talc | 0.025 g. |
| Magnesium stearate | 0.012 g. |

EXAMPLE XI

Effervescent Tablet

| | |
|---|---|
| 4,5-trimethylene-4-isothiazoline-3-one | 0.50 g. |
| Finely pulverized-saccharose | 3.00 g. |
| Sodium bicarbonate | 0.13 g. |
| Citric acid (granular) | 0.22 g. |
| Gum arabic | 0.03 g. |
| Sodium saccharinate | 0.001 g. |
| Stearic acid | 0.01 g. |

-continued

| | |
|---|---|
| Aromatized powder | 0.02 g. |

EXAMPLE XII

Powder for capsules

| | |
|---|---|
| 4,5-trimethylene-4-isothiazoline-3-one | 0.1 g. |
| Corn starch | 0.06 g. |
| Magnesium stearate | 0.01 g. |
| Saccharose | 0.26 g. |

This power is compounded in capsules made of gelatin and titanium dioxide.

EXAMPLE XIII

Intravenous Solution

| | |
|---|---|
| 4,5-trimethylene-4-isothiazoline-3-one | 0.1 g. |
| Sodium chloride | 0.8 g. |
| Citric acid/sodium hydroxide buffer q.s.p. pH = 6 | |
| Sterile demineralized water q.s.p. | 100 ml |

What is claimed is:

1. A 4,5-trimethylene-4-isothiazoline-3-one having the formula

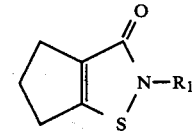

wherein
$R_1$ is selected from the group consisting of hydrogen and linear or branched alkyl having from 1 to 12 carbon atoms, and their salts of a mineral or organic acid.

2. The 4,5-trimethylene-4-isothiazoline-3-one of claim 1 selected from the group consisting of:
(1) 4,5-trimethylene-4-isothiazoline-3-one,
(2) the hydrochloride of (1),
(3) 2-methyl-4,5-trimethylene-4-isothiazoline-3-one,
(4) the hydrochloride of (3),
(5) 2-ethyl-4,5-trimethylene-4-isothiazoline-3-one,
(6) 2-propyl-4,5-trimethylene-4-isothiazoline-3-one,
(7) 2-isopropyl-4,5-trimethylene-4-isothiazoline-3-one,
(8) the hydrochloride of (7),
(9) 2-butyl-4,5-trimethylene-4-isothiazoline-3-one,
(10) the hydrochloride of (9),
(11) 2-isobutyl-4,5-trimethylene-4-isothiazoline-3-one,
(12) 2-tert.butyl-4,5-trimethylene-4-isothiazoline-3-one,
(13) 2-hexyl-4,5-trimethylene-4-isothiazoline-3-one and
(14) 2-octyl-4,5-trimethylene-4-isothiazoline-3-one.

3. The 4,5-trimethylene-4-isothiazoline-3-one of claim 1 wherein $R_1$ is methyl, ethyl, propyl, isopropyl, butyl, isobutyl, tert.butyl, hexyl, octyl or dodecyl.

4. The 4,5-trimethylene-4-isothiazoline-3-one of claim 1 in the form of a salt selected from a hydrochloride, a hydrobromide, a nitrate, a sulfate or a succinate.

5. An anti-bacteria, anti-fungus or anti-acne agent comprising the 4,5-trimethylene-4-isothiazoline-3-one of claim 1.

6. A cosmetic composition comprising in a cosmetically acceptable carrier an effective amount of the 4,5-trimethylene-4-isothiazoline-3-one of claim 1.

7. The cosmetic composition of claim 6 wherein said 4,5-trimethylene-4-isothiazoline-3-one is present in an amount ranging from 0.1 to 10 percent by weight based on the total weight of said composition.

8. A pharmaceutical composition for human or veterinary use comprising in a pharmaceutically acceptable carrier an effective amount of the 4,5-trimethylene-4-isothiazoline-3-one of claim 1.

9. The pharmaceutical composition of claim 8 wherein said 4,5-trimethylene-4-isothiazoline-3-one is present in an amount ranging from 0.1 to 10 percent by weight based on the total weight of said composition.

10. A process for preventing or treating infectious bacterial, fungal or acneal diseases of the epidermis comprising administering to a human an effective amount of a 4,5-trimethylene-4-isothiazoline-3-one having the formula:

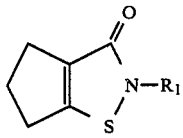

wherein
$R_1$ is selected from the group consisting of hydrogen and linear or branched alkyl having 1 to 12 carbon atoms, and its salt of a mineral or organic acid.

11. The process of claim 10 wherein said 4,5-trimethylene-4-isothiazoline-3-one is selected from the group consisting of:
(1) 4,5-trimethylene-4-isothiazoline-3-one,
(2) the hydrochloride of (1),
(3) 2-methyl-4,5-trimethylene-4-isothiazoline-3-one,
(4) the hydrochloride of (3),
(5) 2-ethyl-4,5-trimethylene-4-isothiazoline-3-one,
(6) 2-propyl-4,5-trimethylene-4-isothiazoline-3-one,
(7) 2-isopropyl-4,5-trimethylene-4-isothiazoline-3-one,
(8) the hydrochloride of (7),
(9) 2-butyl-4,5-trimethylene-4-isothiazoline-3-one,
(10) the hydrochloride of (9),
(11) 2-isobutyl-4,5-trimethylene-4-isothiazoline-3-one,
(12) 2-tert.butyl-4,5-trimethylene-4-isothiazoline-3-one,
(13) 2-hexyl-4,5-trimethylene-4-isothiazoline-3-one and
(14) 2-octyl-4,5-trimethylene-4-isothiazoline-3-one.

12. The process of claim 10 where in said 4,5-trimethylene-4-isothiazoline-3-one $R_1$ is methyl, ethyl, propyl, isopropyl, butyl, isobutyl, tert.butyl, hexyl, octyl or dodecyl.

13. The process of claim 10 wherein said 4,5-trimethylene-4-isothiazoline-3-one is in the form of a salt selected from a hydrochloride, a hydrobromide, a nitrate, a sulfate or a succinate.

14. A 4,5-trimethylene-4-isothiazoline-3-one selected from the group consisting of:
(1) 4,5-trimethylene-4-isothiazoline-3-one,
(2) the hydrochloride of (1),
(3) 2-methyl-4,5-trimethylene-4-isothiazoline-3-one,
(4) 2-isopropyl-4,5-trimethylene-4-isothiazoline-3-one,
(5) 2-butyl-4,5-trimethylene-4-isothiazoline-3-one,
(6) the hydrochloride of (5) and
(7) 2-octyl-4,5-trimethylene-4-isothiazoline-3-one.

15. An anti-bacteria, anti-fungus or anti-acne agent comprising 4,5-trimethylene-4-isothiazoline-3-one.

16. A cosmetic composition comprising in a cosmetically acceptable carrier 4,5-trimethylene-4-isothiazoline-3-one present in an amount ranging from 0.1 to 10 percent by weight based on the total weight of said composition.

17. A pharmaceutical composition for human or veterinary use comprising in a pharmaceutically acceptable carrier, 4,5-trimethylene-4-isothiazoline-3-one present in an amount ranging from 0.1 to 10 percent by weight based on the total weight of said composition.

* * * * *